(12) United States Patent
Yasui

(10) Patent No.: US 8,467,855 B2
(45) Date of Patent: Jun. 18, 2013

(54) SYRINGE NEEDLE GUIDING APPARATUS

(75) Inventor: Norio Yasui, Kamakura (JP)

(73) Assignee: Nory Co., Ltd., Kamakura-shi, Kanagawa (JP)

( * ) Notice: Subject to any disclaimer, the term of this patent is extended or adjusted under 35 U.S.C. 154(b) by 19 days.

(21) Appl. No.: 12/999,179

(22) PCT Filed: Jun. 3, 2009

(86) PCT No.: PCT/JP2009/060189
§ 371 (c)(1),
(2), (4) Date: Dec. 15, 2010

(87) PCT Pub. No.: WO2009/154081
PCT Pub. Date: Dec. 23, 2009

(65) Prior Publication Data
US 2011/0092811 A1 Apr. 21, 2011

(30) Foreign Application Priority Data

Jun. 16, 2008 (JP) .................. 2008-182010
Jul. 23, 2008 (JP) .................. 2008-211175
Nov. 28, 2008 (JP) .................. 2008-328705
May 22, 2009 (JP) .................. 2009-124537

(51) Int. Cl.
*A61B 5/05* (2006.01)
(52) U.S. Cl.
USPC ............... 600/427; 600/476; 600/407
(58) Field of Classification Search
USPC .................. 600/427, 473
See application file for complete search history.

(56) References Cited

U.S. PATENT DOCUMENTS 6,464,646 B1 10/2002 Shalom et al.
7,605,826 B2 * 10/2009 Sauer .................... 345/633
(Continued)

FOREIGN PATENT DOCUMENTS

EP 1982650 A1 10/2008
GB 2303942 A 5/1997
(Continued)

OTHER PUBLICATIONS

JP 11-509748, JP 9-173350, WO 2007/091464 considered to the extent of the translated abstract provided by applicant.

*Primary Examiner* — Unsu Jung
*Assistant Examiner* — Saurel S Selkin
(74) *Attorney, Agent, or Firm* — Jacobson Holman PLLC

(57) ABSTRACT

Provided is a syringe needle guiding apparatus 4 which creates images of a blood vessel 9 which cannot be directly seen with the naked eyes and of a syringe needle 10 inserted into a body, and which includes a monitor 3 allowing the recognition of the three-dimensional relationship between the blood vessel 9 and the needle 10. In the syringe needle guiding apparatus 4 provided here, the blood vessel 9 is seen through by using near infrared rays and also a part of the needle 10, which cannot be seen through because it is inserted into a body, is reproduced in a form of virtual image. A virtually synthesized image of the blood vessel 9 and the needle 10 is displayed on the monitor 3. Then, a target 88 at which the needle 10 is to be inserted, a direction, a distance 12-A, an angle 12-B of the needle with respect to the blood vessel, and the like are displayed in the synthesized image, so that the positional relationship between the blood vessel and the needle 10 is recognized in a three-dimensional manner.

3 Claims, 3 Drawing Sheets

U.S. PATENT DOCUMENTS

| | | |
|---|---|---|
| 2006/0173351 A1 | 8/2006 | Marcotte |
| 2007/0167712 A1 | 7/2007 | Keglovich et al. |
| 2008/0091101 A1 * | 4/2008 | Velusamy et al. ............ 600/427 |

FOREIGN PATENT DOCUMENTS

| | | |
|---|---|---|
| JP | 9-173350 A | 7/1997 |
| JP | 11-509748 A | 8/1999 |
| JP | 2000-316866 A | 11/2000 |
| JP | 2002-507446 A | 3/2002 |
| JP | 2004-267534 A | 9/2004 |
| JP | 2005-066310 A | 3/2005 |
| JP | 2006-130201 A | 5/2006 |
| JP | 2007-512854 A | 5/2007 |
| WO | 2007/091464 A1 | 8/2007 |

* cited by examiner

SYRINGE NEEDLE GUIDING APPARATUS

CROSS-REFERENCE TO RELATED APPLICATIONS

The present patent application is a nationalization of International application No. PCT/JP2009/060189, filed Jun. 3, 2009, published in Japanese, which is based on, and claims priority from, Japanese Patent Applications No. JP 2008-182010, filed Jun. 16, 2008, No. JP 2008-211175, filed Jul. 23, 2008, No. JP 2008-328705, filed Nov. 28, 2008, and No. JP 2009-124537, filed May 22, 2009, all of which are incorporated herein by reference in their entireties.

TECHNICAL FIELD

The present invention relates to a guiding apparatus to facilitate the insertion of a syringe needle into a blood vessel.

BACKGROUND ART

As one of the techniques in inserting a syringe needle into a blood vessel in intravenous injection and blood collection, medical doctors and nurses estimate the location of a blood vessel by observing and/or touching skin and insert a needle. A large portion of this technique, relies on the person's experience and intuition. Thus, the goal of needle insertion is not always achieved certainly by the first insertion.

A cause of such uncertainty in the technique of inserting a needle into a vein is that some blood vessels inside a body cannot be seen directly, and therefore it is difficult to figure out where they are located, how they extend, what kind of shape they have, and so forth. In addition, another cause is that apart of a syringe needle having been inserted into a body cannot be seen with the naked eyes, and therefore the true positional relationship between a blood vessel and the needle cannot be recognized.

To solve these problems, Patent Document 1 discloses an invention that visualizes the state of a blood vessel by use of infrared rays. In addition, Patent Document 2 discloses a method of allowing the state of a blood vessel to be seen with the naked eyes by use of light having a wavelength of 700 to 800 nm. Moreover, Patent Document 3 discloses a method in which a hotspot obtained by an infrared ray detector is assumed as a blood vessel and the location of the hotspot is indicated with pigment or a point light source. Further, Patent Document 4 discloses an apparatus with which the location of the tip of a syringe needle inside a body is estimated based on the shape of the syringe and the estimated location of the tip of the needle is synthesized with an image of a blood vessel and displayed. Furthermore, Patent Document 5 discloses an apparatus with which the location of a vein is detected by use of an ultrasonic wave and a syringe needle is moved forward in the direction of a reflected wave.

PRIOR ART DOCUMENTS

Patent Documents

Patent Document 1: Japanese patent application Kokai publication No. 2004-267534
Patent Document 2: Japanese patent application Kokai publication No. 2000-316866
Patent Document 3: Japanese patent application Kokai publication No. 2002-507446
Patent Document 4: Japanese patent application Kokai publication No. 2006-130201
Patent Document 5: Japanese patent application Kokai publication No. 2005-66310

SUMMARY OF THE INVENTION

Problem to be Solved by the Invention

Nonetheless, any of these conventional techniques for inserting a syringe needle into a blood vessel requires trial-and-error-like operation since it relies on uncertain information obtained through the estimation of the location of a blood vessel by observing and/or touching an outer part of a body, as mentioned above. For instance, Patent Document 4 discloses a technique in which an image is created for a blood vessel, the location of the tip of a needle inserted into a body is estimated, and a synthesized image including the blood vessel and the location of the tip of the needle is displayed. The apparatus described in Patent Document 4 makes it possible to figure out the relationship between the plan position of the blood vessel and the plan position of the tip of the needle; however, the positional relationship therebetween in the depth direction remains unclear.

That is to say, in order to perform injection into a blood vessel, the tip of a needle needs to be fit into and stay inside the blood vessel; however, a planar image alone may lead to a misunderstanding of the positional relationship with the blood vessel. For instance, one may perform injection without recognizing that the tip of a needle has not reached a blood vessel or that the tip has penetrated through the blood vessel. In sum, injection can be performed only when a blood vessel and the tip of a needle are positioned in a three-dimensional manner.

With this background, the present invention aims to provide the following syringe needle guiding apparatus. Specifically, the syringe needle guiding apparatus creates virtual images of a blood vessel that cannot be directly seen with the naked eyes, by seeing through the blood vessel by using of near infrared rays, based on the fact that reduced hemoglobin flowing through veins has a characteristic of absorbing and reflecting a specific infrared ray. In addition, the syringe needle guiding apparatus recognizes the shapes (information) of a syringe and its needle by using of visible light and creates images of a part of needle which has been inserted into a body and cannot be seen through, via virtual reproduction. Moreover, the syringe needle guiding apparatus includes a monitor which can display the three-dimensional positional relationship between the blood vessel and the needle.

A desirable, ideal form of a blood vessel injection supporting apparatus is that a blood vessel and a needle are seen through directly in a three-dimensional image. However, achieving it has many problems in practical use, such as the complication of the apparatus, a possibility of being exposed to radiation due to X-rays or the like for seeing through the needle, a need for troublesome polarized glasses and an apparatus for viewing a three-dimensional image, and the like.

In this respect, the present invention makes it possible to provide a two-dimensional image monitor (motion picture) that provides information as effective as a three-dimensional image in the following manner. Specifically, in the present invention, on assumption that the shape of a syringe needle to be used is identified in advance and with focus placed on the fact that the insertion of a syringe needle into a muscle is pure linear movement, virtual images of the needle and an extended line of the needle are created, and then the needle's direction, target, distance and angle, which are necessary for advancing operation, are displayed in a blood vessel image as depth information.

Means for Solving the Problem

A syringe needle guiding apparatus according to the present invention for achieving the above described object is characterized by comprising: means for creating an image of a blood vessel by using a near infrared ray; means for creating an image of a needle by using visible light; and means for creating a virtual image of the needle inserted into a body and a virtual image of an extended line of the needle.

The above-described syringe needle guiding apparatus is characterized in that a virtual image is created for each of the blood vessel, the needle and the extended line of the needle on the basis of image information on a syringe, the needle and the blood vessel acquired by two cameras so placed as to face the blood vessel and to be parallel to each other, and a synthesized image of the blood vessel, the needle and the extended line of the needle is created for each of viewpoints of the respective cameras.

The above-described syringe needle guiding apparatus is characterized in that when a first image and a second image of the synthesized images are expressed respectively by X-Y coordinate axes and X-Z coordinate axes, an X-axis value of an intersection at which the blood vessel and the extended line of the virtual needle in the second image intersect with each other is marked, as a virtual target at which the needle is to be inserted into the blood vessel, in a location on the blood vessel having the same X-axis value in the first image, and when the extended line of the virtual needle in the first image coincides with the mark through directional manipulation of the syringe, the syringe needle is inserted into the coinciding location.

The above-described syringe needle guiding apparatus is characterized in that the mark and at least one of a distance from a tip of the needle to the mark and an angle of the needle with respect to the blood vessel are displayed in the synthesized images.

The above-described syringe needle guiding apparatus is characterized in that the distance from the tip of the needle to the mark and the angle of the needle with respect to the blood vessel are indicated by a figure having the mark as its center, and the figure is a depth-wise virtual image in which a change of the distance along with movement of the needle is expressed by a change in size of the figure and a change of the angle along with movement of the needle is expressed by a change in shape of the figure.

The above-described syringe needle guiding apparatus is characterized in that an approaching state of the needle to skin is checked by capturing an image of the needle and a shadow cast on the skin by the needle, a moment immediately before the needle comes into contact with the skin is recognized based on a shape of the image, and a warning is displayed on the monitor, or an alert is put out by use of a sound.

The above-described syringe needle guiding apparatus is characterized in that the synthesized images are displayed on a three-dimensional display as three-dimensional images.

Effects of the Invention

As mentioned above, the present invention is an apparatus which creates images of a blood vessel and a needle and recognizes the positional relationship between the blood vessel and the needle. From the present invention, the following effects are expected.

1) A blood vessel can be recognized by using a blood vessel image whose image quality is optimized by using a see-through technology and an image processing technique, instead of relying on the sensitivity of the naked eyes.

2) What kind of shapes blood vessels have and how the blood vessels extend and bend, and so forth can be recognized correctly. Therefore, a suitable blood vessel for needle insertion as well as a suitable part of the blood vessel for the insertion can be selected readily.

3) By the blood vessel recognition described above, the type and size of a syringe needle can be selected in advance.

4) A needle's insertion target, direction and angle which allow the needle and the blood vessel to intersect each other in a three-dimensional space can be figured out precisely.

5) A target (distance, insertion angle and direction) of a syringe needle is displayed in real time in synchronization with the directional manipulation and insertion operation of the needle by a person to perform injection. Hence, simple yet accurate insertion of the needle into a blood vessel can be performed only by the guiding using a monitor.

According to the above, the present invention can provide a significant improvement in any of operability, accuracy and reliability in intravenous injection.

BEST MODES FOR CARRYING OUT THE INVENTION

In the present invention, a virtual image of a blood vessel, which cannot be figured out with the naked eyes, is created by use of near infrared rays. Based on information on a syringe and its needle recognized by visible light or the like, virtual images of the needle inserted into a body and the needle's straight advancing line are created.

Then, the virtual image of the blood vessel and the image of the needle (and a virtually duplicated needle) and the extended line of the needle are displayed on a monitor as a synthesized image (mixed reality) reflecting the actual positional relationship.

Note that the positional relationship between the blood vessel and the needle is to be recognized in three dimensions; hence, the synthesized image is created as images seen from two different points. The two images are displayed on the monitor or image data thereof are recorded.

Then, based on the two sets of image data, the location of the blood vessel as the needle's insertion target, the distance from the needle tip to the target blood vessel, and the angle of the needle with respect to the blood vessel are measured (analyzed using a computer) and displayed on the monitor.

Example 1

Figure 1:
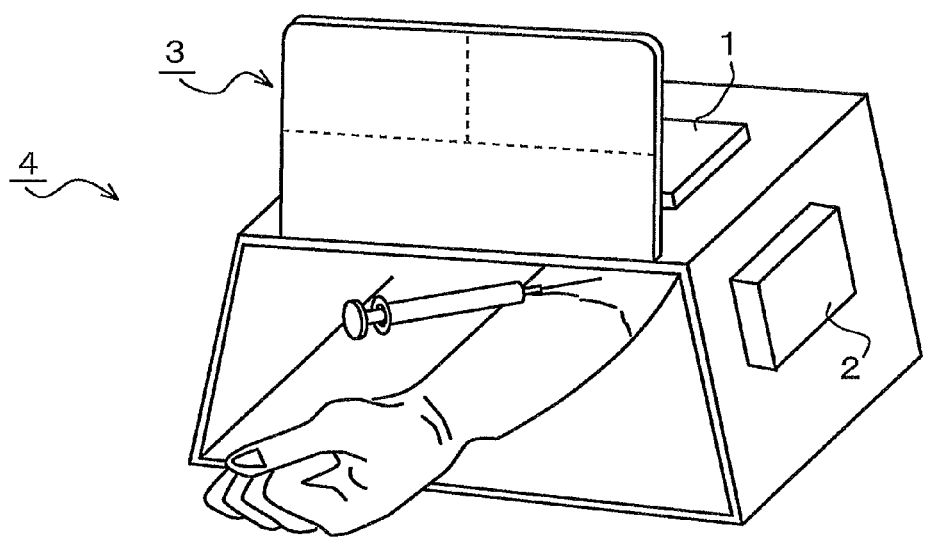
FIG. 1 is a perspective view of the external appearance of a syringe needle guiding apparatus according to an embodiment of the present invention.
Figure 2:
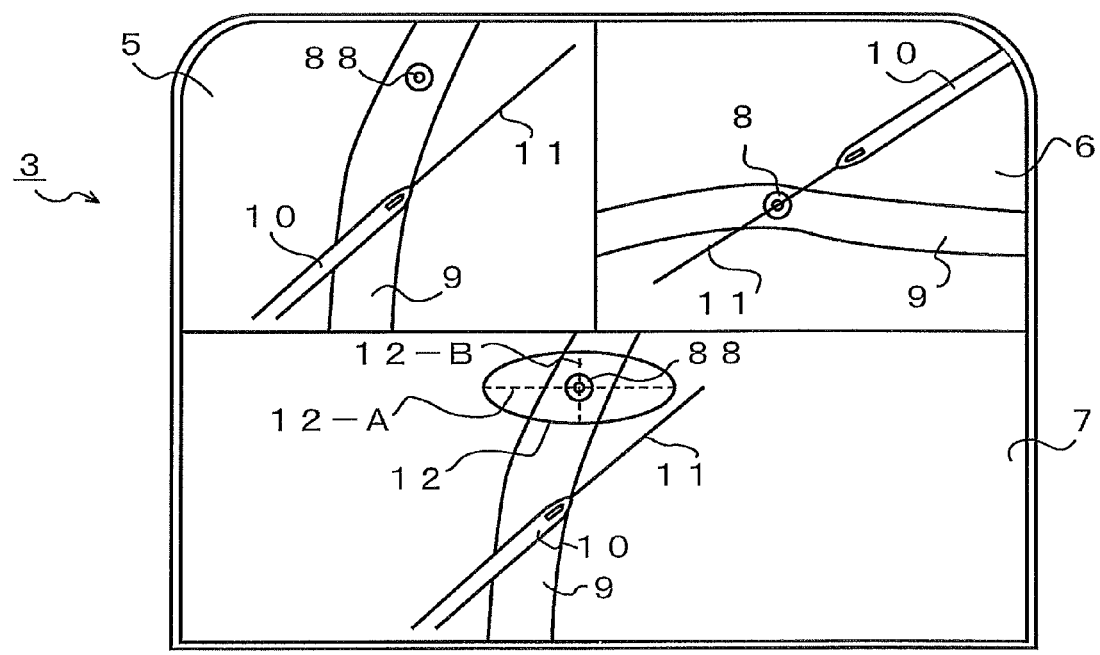
FIG. 2 is a diagram showing an instance of the contents of images on a monitor shown in FIG. 1.

Embodiments of the present invention will be described by referring to the drawings. FIG. 1 is a perspective diagram of an overview of a syringe needle guiding apparatus 4 including built-in cameras, each of which includes a light source of near infrared rays or the like used for capturing images of a blood vessel, and different built-in cameras for capturing images of a syringe and its needle 10.

Each of a planar camera 1 and a lateral camera 2 is a camera functioning as a near infrared camera for capturing an image of a blood vessel as well as a visible light camera for capturing images of a syringe and its needle. The planar camera 1 captures images of a blood vessel 9, the syringe and the needle 10 from above, whereas the lateral camera 2 captures images of the blood vessel 9, the syringe and the needle 10 from a lateral side.

A planar image 5 is an image which is obtained by synthesizing, by using mixed reality technology, images of the blood vessel 9 and the syringe needle 10 captured by the planar camera 1 and an image of a virtual needle 10 and its extended line 11, and displaying in the synthesized image an insertion target 88 in such a location on the blood vessel that the needle 10 is expected to be inserted.

A lateral image 6 is an image displayed as a synthesized image obtained by synthesizing an image captured by the lateral camera 2 and a virtual image by using mixed reality technology, as in the case of the planar image.

Meanwhile, the insertion target 88 in the planar image 5 is obtained by detecting an intersection 8 at which the extended line 11 of the virtual needle and the blood vessel 9 in the lateral image 6 intersect each other on the screen and then by plotting the intersection 8 at the same location on the blood vessel in the planar image 5. The insertion target 88 is displayed in such a way that it moves on the blood vessel 9 in real time along with the directional manipulation of the syringe.

Note that the above-mentioned "insertion target 88" and "same location on the blood vessel" in the planar image 5 are defined as follows.

Assuming that three-dimensional coordinate axes are X, Y and Z, the planar image 5 and the lateral image 6 can be expressed by X-Y coordinates and X-Z coordinates, respectively. The X-axis is a coordinate axis common between the two images. Hence, the same location 88 is defined as a part of the blood vessel in the planar image 5, which is located at the same X coordinate as the X coordinate of the intersection 8 of the extended line 11 of the needle 10 with the blood vessel 8 in the lateral image 6. Incidentally, the insertion target 88 in the planar image 5 is displayed automatically by a video engine program.

A total image 7 is an enlarged version of the planar image 5 focusing on the insertion target 88. This total image 7 indicates, with an ellipse, a distance from the needle tip to the insertion target 88 as well as an angle at which the extended line 11 of the needle intersects the blood vessel 9 in the lateral image 6. Although an ellipse is used in Example 1, the shape is not limited and may be a rectangle or a star.

Next, a distance 12-A and an angle 12-B indicate the distance from the needle tip to the insertion target 88 and the angle of the needle with respect to the blood vessel, respectively, which are acquired through the measurement (computer analysis) of the image data of both the planar and lateral images.

The ellipse is displayed with the insertion target 88 as its center. The distance 12-A is expressed by the size of the diameter of the ellipse along its horizontal axis. The angle 12-B is expressed by the size of the diameter of the ellipse along its vertical axis, which is a product of an angular coefficient and the size of the horizontal-axis diameter indicating the distance.

In general, a certain needle angle is necessary in the insertion of a syringe needle 10 into a blood vessel 9. The angle 12-B is an angle at which the extended line 11 of the virtual needle and the blood vessel 9 in the lateral image 6 intersect each other. Assuming that the angle 12-B is preferably 30 degrees, the angular coefficient is 1 when the angle is 30 degrees. With the angular coefficient of 1, the size of the diameter of the ellipse along its vertical axis is equal to the size of the diameter of the ellipse along its horizontal axis indicating the distance 12-A. In other words, a setting is made such that while the angle is kept at an appropriate value, or 30 degrees, the ellipse always shows a circle regardless of the distance.

For this reason, the indication of the angle is set as follows. Specifically, the horizontal-axis diameter indicating the distance 12-A is used as a reference. When the angle is larger than 30 degrees, the ellipse becomes a horizontally elongated ellipse whose size along the vertical axis is smaller than that along the horizontal axis in inverse proportion. The ellipse becomes a vertically elongated ellipse when the angle is smaller than 30 degrees.

Figure 3:
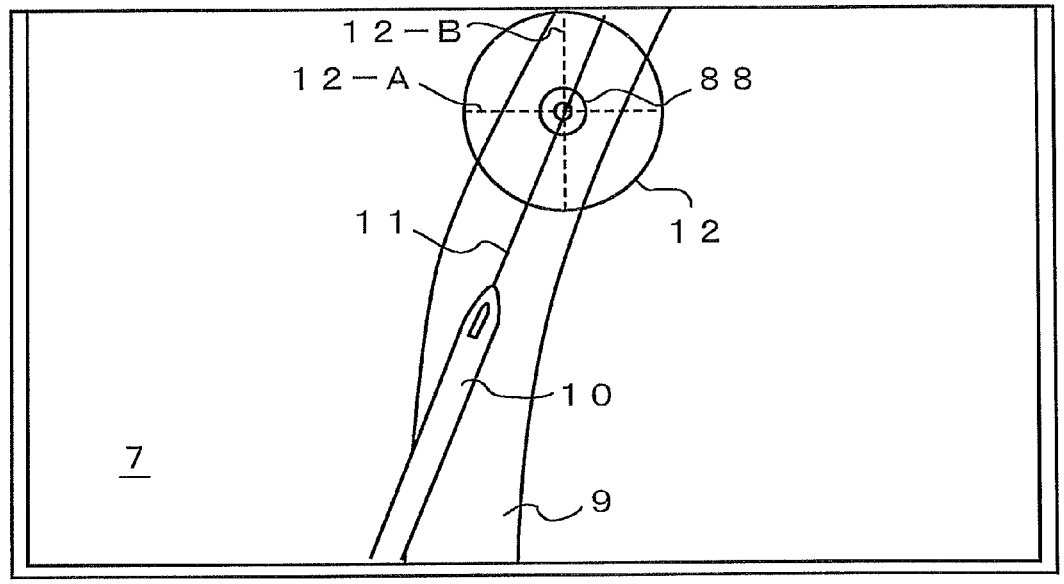
FIG. 3 is a diagram showing an instance of the content of a total image, which is a part of FIG. 2.

FIG. 3 shows an instance of what is displayed in the total image 7. FIG. 3 shows a state where the extended line 11 of the needle intersects the insertion target 88, the angle is expressed with a circle, and the syringe needle can therefore be inserted in a body.

In other words, FIG. 3 shows a state where the extended line 11 of the virtual needle is caused to coincides with the insertion target 88 by the directional manipulation of the syringe performed by hand, and a location in a three-dimensional space in which the blood vessel and the extended line of the virtual needle intersect each other is detected.

Moreover, FIG. 3 shows a state where the directional manipulation of the syringe has resulted in the displaying of a circle indicating an appropriate insertion angle of the needle with respect to the blood vessel.

Thus, as the syringe needle is inserted straight into the body from the state in FIG. 3, the circle becomes smaller and smaller and becomes a dot while keeping its circular shape. Finally, the needle comes to be inserted into the blood vessel.

Next, functions of the monitor 3 will be described. Note that a main purpose of having the planar image 5 and the lateral image 6 is to acquire, from image data thereof, depth information (three-dimensional information) such as an insertion target, a distance, a direction and an angle.

In Example 1, the planar image 5 and the lateral image 6 are displayed on the monitor for the sake of explaining the technical idea of the present invention. However, the images do not necessarily have to be displayed on the monitor 3, and may only need to be figured out and recorded.

The total image 7 is obtained by putting together the information on the planar image 5 and the lateral image 6, and additionally displaying the depth information (three-dimensional information) necessary for blood vessel injection on the planar image 5. Thus, a person to perform injection only needs pay attention to the monitor with this total image and guide the needle in order to perform accurate and safe blood vessel injection.

As mentioned above, in Example 1, three screens are displayed on the monitor 3 for illustrative purpose. However, when it comes to actual operation, it is preferable to display only a screen of the total image 7 on the entire monitor.

Now, it is necessary to alert a person to perform injection that the needle has become near to the skin, so that the skin would not be damaged carelessly with the needle when the person to perform injection performs a procedure while paying attention to the monitor.

To do so, the visible light cameras (provided to the planar camera 1 and the lateral camera 2) are used to capture images of the needle 10 and a shadow cast onto the skin by the needle 10. Then, based on the shape which the needle 10 and the shadow together form, an approaching state is detected (automatically detected using a video engine program). The detected result is displayed on the monitor; otherwise, the person to perform injection is warned by a sound.

Figure 4:
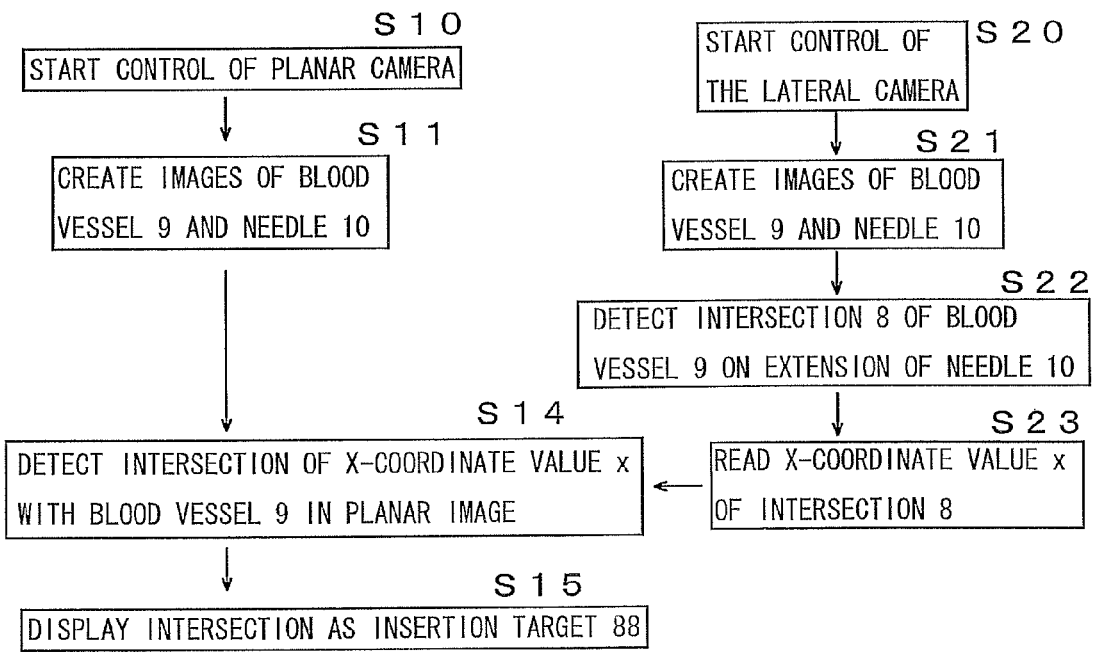
FIG. 4 is a chart showing a control flow for determining an insertion target.

FIG. 4 shows a control flow for determining an insertion target 88 in a planar image 5. Description of the control flow will be briefly provided below. First, a step of starting control of the lateral camera (S20), a step of creating images of a blood vessel 9 and a needle 10 (S21), and a step of detecting an intersection 8 of an extended line 11 of the needle 10 with the blood vessel 9 (S22) are performed to read an X-coordinate value x of the intersection 8 (S23). In the meanwhile, a step of starting control of the planar camera (S10) and a step of creating images of the blood vessel 9 and the needle 10 (S11) are performed to acquire a planar image 5 in advance. Here, control is performed to display, as an insertion target 88, a point at which the X-coordinate value in the planar image 5 is x and intersects with the blood vessel 9. Thereby, an insertion target 88 is determined.

Figure 5:
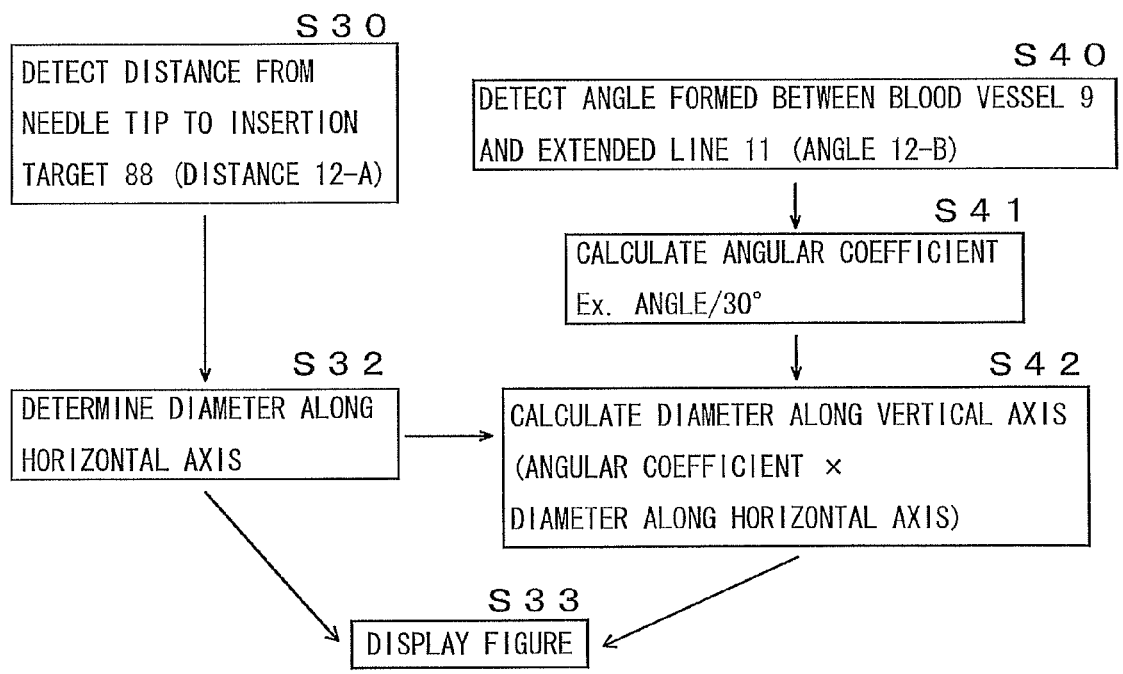
FIG. 5 is a chart showing a control flow for calculating the shape of a figure indicating the positional relationship between an insertion target and the tip of a needle.

FIG. 5 shows a control flow for determining the shape of a figure to be displayed in a total image 7, i.e., a figure to indicate depth information (three-dimensional information) necessary for blood vessel injection. Description of the control flow will be briefly provided below. Here, an instance is shown where an ellipsoidal figure is displayed. First, there are provided: a step of detecting a distance 12-A from a needle tip to an insertion target 88 (S30); and a step of determining the length of the diameter of an ellipse along its horizontal axis on the basis of the distance 12-A (S32).

In the meanwhile, there are provided: a step of detecting an angle 12-B formed between a blood vessel 9 and an extended line 11 of a needle 10 (S40); a step of calculating an angular coefficient by dividing the angle 12-B by an optimal angle (e.g., 30°) (S41); and a step of determining the length of the diameter of the ellipse along its vertical axis by multiplying the diameter of the ellipse along its horizontal axis obtained in Step 32 by the angular coefficient (S42).

The shape of the ellipse is determined based on the diameters along the horizontal and vertical axes thus obtained, and displayed in a total image 7 (S33). This control makes it possible to obtain information on the three-dimensional relative locations of the needle tip and the blood vessel. Accordingly, a highly practical syringe needle guiding apparatus can be provided.

Example 2

Example 2 is a case where the monitor for a total image in Example 1 displays a three-dimensional image. Although polarized glasses and/or the like are required, the image data (including the insertion target 88 and the extend line of the needle) of both the planar image 5 and the lateral image 6 is displayed on a three-dimensional display.

Hereinabove, examples are described. However, embodiments reflecting the technical idea of the present invention are not limited to the aforementioned examples. Moreover, the video engine program that automatically recognizes image data such as an insertion target, a distance, an angle and synthesis and makes notification using images can be changed in various ways. The procedure for carrying out the present invention and the claims of the present invention are not to be limited by embodiments of the program and the like.

INDUSTRIAL APPLICABILITY

A syringe needle guiding apparatus of the present invention which creates virtual images of a blood vessel and a needle and displays the relationship between the blood vessel and the needle in terms of depth is useful in intravenous injection. In addition, the syringe needle guiding apparatus is also useful as a guiding support apparatus used in such occasions as blood collection, blood transfusion, intravenous drip as well as when a femoral vein/artery, a medial femoral vein/artery, a subclavian vein/artery, a median vein/artery, or the like is to be punctured with a medical device such as a needle, a catheter or a stent.

EXPLANATION OF REFERENCE NUMERALS

1 planar camera
2 lateral camera
3 monitor screen
4 syringe needle guiding apparatus
5 planar image
6 lateral image
7 total image
8 intersection (a point at which an extended line of a needle intersects a blood vessel in a lateral image)
9 blood vessel
10 needle, virtual needle
11 extended line of needle (advancing virtual line)
12 circle/ellipse indicating distance and angle
12-A length of circle/ellipse along its horizontal axis (indicating a distance from a needle tip to an insertion target)
12-B length of circle/ellipse along its vertical axis (indicating an angle of a needle with respect to a blood vessel)
88 insertion target

What is claimed is:

1. A method of operating apparatus for guiding insertion of a needle of a syringe into a blood vessel in a body such that part of the needle is inserted into the body and part of the needle remains outside the body, the apparatus including: a planar camera and a lateral camera, each of which includes a built-in near infrared camera and a visible light camera and which are so placed as to face the blood vessel and to be parallel to each other; a monitor, and a computer, the method characterized by comprising the steps of:

capturing images of the blood vessel, the syringe, and the part of the needle of the syringe remaining outside the body with the planar camera and with the lateral camera, images of the part of the needle inserted into the body being unable to be captured by the visible light cameras of the planar camera and the lateral camera, and images of the blood vessel being captured only by the near infrared cameras of the planar camera and the lateral camera;

obtaining a planar image forming an X-Y coordinate plane by overlaying the images of the blood vessel, the syringe, and the needle of the syringe;

obtaining a lateral image forming an X-Z coordinate plane by overlaying the images of the blood vessel, the syringe, and the needle of the syringe, the lateral image having a common X-axis with the planar image;

displaying the planar image and the lateral image on the monitor;

using the computer to detect the image of the needle of the syringe from each of the planar image and the lateral image displayed on the monitor, and to perform a process of displaying, on a line extending from each image of the needle of the syringe, an image of the part of the needle inserted into the body and a straight extended line representing advancing of the needle, by:

using the computer to detect, in the lateral image, an X-coordinate value of an intersection at which the extended line of the needle of the syringe and the blood vessel intersects each other;

using the computer to read the X-coordinate value of the intersection on the X-axis; and using the computer to detect, from the planar image, a point which has the same value as the X-coordinate value of the intersection and which is present on the blood vessel, and to perform a process of displaying the point on the monitor as an insertion target, wherein the step of detecting the X-coordinate value, the step of reading the X-coordinate value, and the step of performing the process of displaying the insertion target are performed repeatedly.

2. The method of operating a syringe needle guiding apparatus according to claim 1, characterized by further comprising the steps of:

using the computer to calculate a distance from a tip of the needle of the syringe to the insertion target, for the planar image and the lateral image;

using the computer to detect an angle formed between the blood vessel and the extended line of the needle of the syringe in the lateral image; and using the computer to display the distance and the formed angle in the planar image.

3. The method of operating a syringe needle guiding apparatus according to claim 2, characterized by further comprising the steps of:

using the computer to form an ellipsoidal figure having a horizontal axis, a vertical axis, a diameter along the horizontal axis, and a diameter along the vertical axis, the insertion target being at the center of the ellipsoidal figure, and wherein the diameter of the ellipsoidal figure along the horizontal axis corresponds to the distance from the tip of the needle of the syringe to the insertion target in the planar image and the lateral image, and also the diameter along the vertical axis corresponds to the angle formed between the blood vessel and the extended line of the needle in the lateral image; and using the computer to display the elliptical figure in the planar image.

\* \* \* \* \*